(12) United States Patent
Yanamoto

(10) Patent No.: US 10,849,344 B2
(45) Date of Patent: Dec. 1, 2020

(54) SPROUTED CEREAL, METHOD FOR MANUFACTURING SAME, FOOD PRODUCT CONTAINING SAME, AND BDNF PRODUCTION ACCELERATOR

(71) Applicant: Hiroji Yanamoto, Osaka (JP)

(72) Inventor: Hiroji Yanamoto, Osaka (JP)

( * ) Notice: Subject to any disclaimer, the term of this patent is extended or adjusted under 35 U.S.C. 154(b) by 316 days.

(21) Appl. No.: 15/690,048

(22) Filed: Aug. 29, 2017

(65) Prior Publication Data

US 2017/0354173 A1 Dec. 14, 2017

Related U.S. Application Data

(63) Continuation of application No. 14/005,390, filed as application No. PCT/JP2012/057083 on Mar. 19, 2012, now Pat. No. 9,775,370.

(30) Foreign Application Priority Data

Mar. 17, 2011 (JP) .................. 2011-058645

(51) Int. Cl.
  *A61K 36/899* (2006.01)
  *A23L 7/10* (2016.01)
  *A23L 7/152* (2016.01)

(52) U.S. Cl.
  CPC ............... *A23L 7/101* (2016.08); *A23L 7/152* (2016.08); *A61K 36/899* (2013.01)

(58) Field of Classification Search
  None
  See application file for complete search history.

(56) References Cited

U.S. PATENT DOCUMENTS

| | | | |
|---|---|---|---|
| 4,116,666 | A | 9/1978 | Willard, Sr. |
| 5,330,964 | A | 7/1994 | Alesi, Jr. |
| 5,472,730 | A | 12/1995 | Saikusa et al. |
| 6,433,019 | B1 | 8/2002 | Nawa |
| 2004/0248737 | A1 | 12/2004 | Matsugu et al. |
| 2006/0045924 | A1 | 3/2006 | Chen et al. |
| 2007/0015663 | A1 | 1/2007 | Matsugu et al. |
| 2007/0190222 | A1 | 8/2007 | Shinmura et al. |
| 2008/0286435 | A1 | 11/2008 | Fukumori et al. |
| 2011/0151086 | A1 | 6/2011 | Fukumori et al. |
| 2011/0217438 | A1 | 9/2011 | Ando et al. |

FOREIGN PATENT DOCUMENTS

| | | |
|---|---|---|
| JP | 06-062670 | 3/1994 |
| JP | 07-213252 | 8/1995 |
| JP | 2002-045135 | 2/2002 |
| JP | 2003-125716 | 5/2003 |
| JP | 2003-230364 | 8/2003 |
| JP | 2003-252712 | 9/2003 |
| JP | 2005-013029 | 1/2005 |
| JP | 2005-087205 | 4/2005 |
| JP | 2005-168444 | 6/2005 |
| JP | 2005-341879 | 12/2005 |
| JP | 2007-049947 | 3/2007 |
| JP | 2008-113599 | 5/2008 |
| JP | 2008-212011 | 9/2008 |
| JP | 2008-212013 | 9/2008 |
| JP | 2008-307045 | 12/2008 |
| KR | 2009014802 | 2/2009 |
| WO | 99/38534 | 8/1999 |
| WO | 2010/106611 | 9/2010 |
| WO | 2011/010522 | 1/2011 |

OTHER PUBLICATIONS

Tomoyuki Fujii, "Engineering studies on high-pressure induced transformation of rice", Annual Report/ the Iijima Memorial Foundation for Promotion of Food Science and Technology, Aug. 2006, vol. 2004, pp. 70 to 75; English summary; Cited in International Search Report.
International Search Report dated Jun. 5, 2012 filed in PCT/JP2012/057083.
Zafra et al. "Interplay between glutamate and y-aminobutyric acid transmitter systems in the physiological regulation of brain-derived neurotrophic factor and nerve growth factor synthesis in hippocampal neurons," Proc.Natl.Acad.Sci.USA, vol. 88, pp. 10037-10041, Nov. 1991; Cited in Japanese Office Action dated Jun. 17, 2014 issued in the corresponding Japanese patent application No. 2013-504791.
Concise explanation of relevance of the research paper: Zafra et al. "Interplay between glutamate and y-aminobutyric acid transmitter systems in the physiological regulation of brain-derived neurotrophic factor and nerve growth factor synthesis in hippocampal neurons," Proc.Natl.Acad.Sci.USA, vol. 88, pp. 10037-10041, Nov. 1991.

*Primary Examiner* — Terry A McKelvey
*Assistant Examiner* — Catheryne Chen
(74) *Attorney, Agent, or Firm* — Rankin, Hill & Clark LLP

(57) ABSTRACT

The invention relates to a novel technique for germinating a sproutable food such as rice, other types of cereals, or seeds. Provided is a novel germination technique capable of increasing a content of glutamate, accelerating an enrichment of gamma-aminobutyric acid, and exerting excellent functionality for the body, and a novel functional food material or pharmaceutical agent. A sprouted cereal is produced by soaking the cereal in a soaking solution prepared by addition of at least one carbonate selected from alkali metal carbonate, and alkaline earth metal carbonate to water to make the cereal absorb the soaking solution, followed by allowing the cereal to germinate under predetermined conditions.

11 Claims, 13 Drawing Sheets

|  | UMAMI | FLAVOR |
|---|---|---|
| TEST RICE | 2.4±0.7* | 2.4±0.7* |
| SPROUTED BROWN RICE IN WATER | 1.7±0.7 | 1.4±0.7 |

SPROUTED CEREAL, METHOD FOR MANUFACTURING SAME, FOOD PRODUCT CONTAINING SAME, AND BDNF PRODUCTION ACCELERATOR

TECHNICAL FIELD

The present invention relates to a novel germination method for sprouted brown rice, sprouted cereals, and other sproutable food materials (hereinafter, collectively referred to as sproutable food materials), and to food materials or pharmaceutical agents obtained therefrom.

BACKGROUND ART

It has been known that brown rice or wheat germ increases its gamma-aminobutyric acid content when being in contact with aqueous neutral or acidic solution in the range of appropriate temperature. For example, Patent Document 1 proposes a technique for producing sproutable food materials having an enriched content of gamma-aminobutyric acid by mixing rice brans or wheat embryos with buds with organic acid or inorganic acid to adjust their pH levels to 2.5 to 7.5, preferably 3.0 to 7.0, more preferably 5.5 to 6.0, in a region of weak to strong acidity, and soaking them in an aqueous solution adjusted at a temperature of 50° C. or lower (see Patent Document 1). In other words, the document describes a technique for enrichment of gamma-aminobutyric acid by soaking a specific sproutable food material in an aqueous neutral or acidic solution kept at an appropriate temperature to germinate the sproutable food material.

Cereals cause a germination reaction when being subjected to appropriate moisture and temperature conditions, thereby being softened to be easier to be eaten. However, the appropriate moisture and temperature conditions allow indigenous microorganisms (microorganisms) on the surface of cereals to grow all at once and emit bad smells. Thus, the germination process brings significant adverse effects that impair the original taste of sprouted cereals, and such adverse effects have not been successfully avoided up to now. One of measures for suppressing an unpleasant smell generated in the germination process is roasting after the germination. However, the roasting does not remove microorganisms. On the other hand, various kinds of germination procedures have been conducted to improve the taste of cereals while suppressing the generation of a smell by using some chemicals or the like to prevent the growth of microorganisms generated due to the germination.

A technique for improving the germination process has been proposed. Modifications of such a technique have been proposed such that, for example, chlorine water having sterilization and disinfection activities, a salt solution (saline) or an aqueous acidic solution having bacteriostatic and anti-microbial activities can be used to avoid an unpleasant smell or prevent a food taste from being deteriorated. In general, microorganisms prefer neutral or alkaline conditions rather than acidic conditions during proliferation. For example, one of traditional food preservation techniques is to place a pickled "ume" in a packed lunch or the like. The pickled "ume" contains "sodium chloride" with bacteriostatic activity and "citric acid" serving as an acidic material, and can suppress the growth of microorganisms and keep the quality of food for a certain period of time. However, the chlorine or salt water penetrates into the food material. As a result, there is a problem in that the food material may cause a specific smell or, in the case of salt water, the sproutable food material may have an increased salt concentration.

As an attempt to suppress the growth of microorganisms in the germination process by using salt water (an aqueous sodium chloride solution), Patent Document 2 proposes a technique for germination while suppressing the growth of microorganisms by using an aqueous solution containing at least sodium chloride, or by using deep-sea water (sea water). The solution of sodium chloride in pure water or the deep-sea water has a pH value in the range of, in general, a neutral region that extends from weak acidity to weak alkalinity (pH 6.0 to 8.0).

As an attempt to suppress the growth of microorganisms during the germination process by adjusting the pH of the aqueous sodium bicarbonate solution to acidic, Patent Document 3 describes a technique using an aqueous solution having a pH of 3.0 to 6.0 adjusted with organic acid or inorganic acid. In addition, Patent Document 4 describes a technique using an aqueous solution having an adjusted pH of 3.7 to 4.1. Another technique has been also reported for suppressing the growth of microorganisms; the technique directly restricts the amount of water to be supplied for germination to reduce the generation of a bad smell due to the growth of microorganisms attached on the surface layer of cereals. For example, Patent Document 5 describes a method for reducing the content of water to be added to cereals.

As described above, the growth of microorganisms and the generation of characteristic smells concomitant therewith can be successfully suppressed by the technique using an aqueous acidic solution, a salt solution (at neutral), or a limited amount of water. However, the successful suppression does not lead to an enrichment of glutamate in sprouted cereals to aggressively increase the content of delicious taste (so-called "umami") ingredients in sproutable food materials. In addition, the successful suppression does not lead to an accelerated enrichment of gamma-aminobutyric acid in cereals, or does not lead to the expression of novel functionality based on the production of novel BDNFs for the brain and the body.

Glutamate, one of delicious taste (umami) ingredients, can be provided as a raw material of gamma-aminobutyric acid in the germination process of cereals. Patent Document 6 describes a technique using an aqueous solution containing glutamate in germination and a roasting treatment at high temperature after the germination to prevent cereals from having a decreased glutamate content and a deteriorated taste due to microorganisms.

As a germination technique involving addition of glutamate into an aqueous solution, for example, the Patent Document 7 proposes a method for enrichment of gamma-aminobutyric acid using an enzyme (glutamate decarboxylase reaction) contained in beans by mixing the glutamate-containing food material with the beans. Patent Document 8 proposes a technique for accelerating an enrichment of gamma-aminobutyric acid by addition of an extract from tea leaves, a glutamate-containing food material, into an aqueous solution for germination.

In other words, these techniques are provided for accelerating an enrichment of gamma-aminobutyric acid by addition of glutamate serving as a raw material of gamma-aminobutyric acid, a food material containing glutamate, or an extract of the food material in a germination process of a sproutable food material. However, as described in Examples below, the use of these techniques does not lead to an increase in glutamate content after germination more than one before the germination.

An aqueous sodium bicarbonate solution has been known to have anti-microbial properties. In addition, as described in Patent Documents 9 and 10, an aqueous sodium bicarbonate solution and an aqueous sodium sesquicarbonate solution have been known to work as herbicides that suppress the growth of plants.

CITATION LIST

Patent Literatures

Patent Document 1: JP-A-07-213252
Patent Document 2: JP-A-2003-230364
Patent Document 3: JP-A-2002-45135
Patent Document 4: JP-A-2003-125716
Patent Document 5: JP-A-2008-307045
Patent Document 6: JP-A-2003-179101
Patent Document 7: JP-A-2008-212011
Patent Document 8: JP-A-2008-212013
Patent Document 9: U.S. Pat. No. 5,330,964
Patent Document 10: JP-A-2003-252712

DISCLOSURE OF THE INVENTION

Problems to be Solved by the Invention

Although an enrichment of gamma-aminobutyric acid in a sproutable food material can be accelerated at much expense in cost, time, and effort by addition of glutamate into water that supplies the glutamate from the outside in a germination process, such a kind of operation does not lead to suppression of the growth of microorganisms or an increase in content of glutamate. Such a kind of operation does not lead to an improvement in delicious taste compared with one before the germination. That is, it has been demanded to provide a novel method for producing a sprouted food material, or a new functional food material or a pharmaceutical agent produced by such a method, which can improve delicious taste by glutamate enrichment and accelerate an enrichment of gamma-aminobutyric acid, while reducing the growth of microorganisms and smells generated in a germination process and suppressing a decrease in food taste. In addition, it has been demanded to provide a novel technique for producing a functional food material and a functional food material obtained by such a technique, or to develop a pharmaceutical agent, which accelerate the production of BDNF in the body by administration of any food material to the body and exhibit various functionalities.

In view of the above circumstances, the present inventor has conducted intensive studies to develop a method for reducing a smell generated in a germination process of a sproutable food material, improving delicious taste by a highly enrichment of glutamate, and accelerating an enrichment of gamma-aminobutyric acid having functionality preferable to the living body; a technique for producing a novel functional sproutable food material, the technique being capable of exerting new functionality of accelerating the production of BDNF in the body by application of a food material produced by the method, which has been never found until now; and a food material or pharmaceutical agent obtained by the technique.

Consequently, the present inventor has found a method for producing a sproutable food material having new properties and functionality, which have never been anticipated, such as reduction of a smell, a highly enrichment of glutamate or gamma-aminobutyric acid, and accelerated production of BDNF in the body, by soaking in an aqueous alkaline solution containing at a predetermined concentration of sodium bicarbonate ($NaHCO_3$) instead of pure water, tap-water, an acidic solution, or an aqueous sodium chloride solution for germination. There has been no report representing any germination method for exerting new functionality, as provided by the present invention, obtained by the use of an aqueous sodium bicarbonate solution or an aqueous sesquisodium carbonate solution prepared from sodium bicarbonate and sodium carbonate (described later) for supply of water in a germination process. The new functionality includes an enrichment of glutamate in a sproutable food material, an acceleration of gamma-aminobutyric acid enrichment, and an acceleration of BDNF production in the body due to administration of a food material obtained by the method.

The present invention has been completed based on the above findings.

An object of the invention is to develop a method for manufacturing a food material using cereals as a raw material to reduce a smell generated in a germination process, highly enrich glutamate as a delicious taste ingredient, accelerate an enrichment of gamma-aminobutyric acid, and accelerate BDNF production in the body, and to provide a new food material or pharmaceutical agent obtained by the method.

Solutions to the Problems

The object of the invention described above is achieved by the following means.

(1) That is, the present invention is a sprouted cereal produced by soaking the cereal in a soaking solution having a hydrogen carbonate ion concentration of 0.012 to 0.12 mol/l prepared by addition of at least one carbonate selected from alkali metal carbonate, alkaline earth metal carbonate, and ammonia carbonate to water to make the cereal absorb the soaking solution, followed by allowing the cereal to germinate under predetermined conditions.

(2) The present invention is a sprouted cereal as described in (1), in which pH of the soaking solution ranges from 8.0 to 10.0.

(3) The present invention is a sprouted cereal as described in (1) or (2), in which the carbonate is sodium carbonate, sodium bicarbonate, or sesquisodium carbonate.

(4) The present invention is a sprouted cereal as described in any one of (1) to (3), in which a glutamate content of the sprouted cereal is 1.1 to 2.3 times greater than a glutamate content of a sprouted cereal germinated under the same conditions except that the latter is germinated without addition of the carbonate, when measured by a reference measurement method.

(5) The present invention is a sprouted cereal described in any one of (1) to (4), in which the cereal is brown rice, and a glutamate content of the brown rice is 25 to 100 mg/100 g when measured by a reference measurement method.

(6) The present invention is a sprouted cereal produced by soaking the cereal in the soaking solution having a hydrogen carbonate ion concentration of 0.012 to 0.06 mol/l prepared by addition of at least one carbonate selected from alkali metal carbonate, alkaline earth metal carbonate, and ammonium carbonate to water to make the cereal absorb the soaking solution, followed by allowing the cereal to germinate under predetermined conditions.

(7) The present invention is a sprouted cereal as described in (6), in which pH of the soaking solution ranges from 8.0 to 10.0.

(8) The present invention is a sprouted cereal as described in (6) or (7), in which the carbonate is selected from sodium carbonate, sodium bicarbonate, or sesquisodium carbonate.

(9) The present invention is a sprouted cereal as described in any one of (6) to (8), in which a gamma-aminobutyric acid content of the sprouted cereal is 1.3 to 2.1 times greater than a gamma-aminobutyric acid content of a sprouted cereal germinated under the same conditions except that the latter is germinated without addition of the carbonate, when measured by a reference measurement method.

(10) The present invention is a sprouted cereal as described in any one of (6) to (9), in which the cereal is brown rice, and a gamma-aminobutyric acid content of the sprouted brown rice is 15 to 44 mg/100 g when measured by a reference measurement method.

(11) The invention is a food product that contains at least one type of the sprouted cereals as described in any one of (1) to (10).

(12) The present invention is a sprouted cereal as described in any one of (1) to (4) and (6) to (9), including, as an effective ingredient for a BDNF production accelerator, at least one of the sprouted cereals selected from a group consisting of brown rice, glutinous rice, red rice, black rice, Indica rice, *Javanica* rice, peas (endo mame), broad beans, black beans (kuromame), parched beans, adzuki beans, snap (kidney) beans, safflower kidney beans, peas (endo mame), peanuts, black soybeans (kuro daizu), and soybeans.

(13) The present invention is the BDNF production accelerator as described in (12), including a weight suppressing agent, an antiobesity agent, an appetite suppressing agent, a glucose-metabolism improving agent, a fat metabolism improving agent, an improving agent for cognitive or memory ability, an antidepressant/antianxiety agent, or a listless improving agent.

(14) The present invention is a method for producing a sprouted cereal, the method including the steps of: soaking the cereal in a soaking solution having a hydrogen carbonate ion concentration of 0.012 to 0.12 mol/l prepared by addition of at least one carbonate selected from alkali metal carbonate, alkaline earth metal carbonate, and ammonia carbonate to water to make the cereal absorb the soaking solution; and allowing the cereal absorbing the solution in the previous step to germinate under predetermined conditions.

(15) The present invention is a method for producing a sprouted cereal as described in (14), in which pH of the soaking solution ranges from 8.0 to 10.0.

(16) The present invention is a method for producing a sprouted cereal as described in (14) or (15), in which the carbonate is sodium carbonate, sodium bicarbonate, or sesquisodium carbonate.

(17) The present invention is a method for producing a sprouted cereal as described in any one of (14) to (16), in which a glutamate content of the sprouted cereal is 1.1 to 2.3 times greater than a glutamate content of a sprouted cereal germinated under the same conditions except that the latter is germinated without addition of the carbonate, when measured by a reference measurement method.

(18) The present invention is a method for producing a sprouted cereal as described in any one of (14) to (17), in which the cereal is brown rice and a glutamate content of the brown rice is 25 to 100 mg/100 g when measured by a reference measurement method.

(19) The present invention is a method for producing a sprouted cereal, the method comprising the steps of: soaking the cereal in the soaking solution having a hydrogen carbonate ion concentration of 0.012 to 0.06 mol/1 prepared by addition of at least one carbonate selected from alkali metal carbonate, alkaline earth metal carbonate, and ammonium carbonate to water to make the cereal absorb the soaking solution; and allowing the cereal to germinate under predetermined conditions.

(20) The present invention is a method for producing a sprouted cereal as described in (19), in which pH of the soaking solution ranges from 8.0 to 10.0.

(21) The present invention is a method for producing a sprouted cereal as described in (19) or (20), in which the carbonate is sodium carbonate, sodium bicarbonate, or sesquisodium carbonate.

(22) The present invention is a method for producing a sprouted cereal as described in any one of 09) to (21), in which a gamma-aminobutyric acid content of the sprouted cereal is 1.3 to 2.1 times greater than a gamma-aminobutyric acid content of a sprouted cereal germinated under the same conditions except that the latter is germinated without addition of the carbonate, when measured by a reference measurement method.

(23) The present invention is a method for producing a sprouted cereal as described in any one of (19) to (22), in which the cereal is brown rice, and a gamma-aminobutyric acid content of the sprouted brown rice is 15 to 44 mg/100 g when measured by a reference measurement method.

Effects of the Invention

The invention has the following expected advantages: (a) A smell particular to proliferative microorganisms generated in a process of manufacturing a sproutable food material is reduced, so that the sproutable food material having improved delicious taste can be obtained. (b) In the conventional germination method using water, a germination process causes a decrease in content of glutamate, a principle ingredient for delicious taste, compared with the content thereof before germination. In contrast, the present method causes an increase in glutamate content, so that a sproutable food material having excellent delicious taste can be obtained. (c) A sproutable food material in which an enrichment of gamma-aminobutyric acid is accelerated can be obtained. (d) Eating a food material of the present invention leads to expected health-promoting effects, i.e., an unprecedented memory enhancement effect, an unprecedented appetite suppression (weight suppression) effect, a hypoglycemic effect (improvement of glucose metabolism), a fat metabolism improvement effect, and the like.

Furthermore, the invention also has the following expected advantages: (e) A sproutable food material having new functionality of accelerating the production of BDNF in the body can be produced. (f) Administration of a food material or a pharmaceutical agent obtained by such a production to an organism leads various kinds of preferred functionality and health promoting action due to an increase in BDNF production in the body.

DESCRIPTION OF EMBODIMENTS

Figure 1:
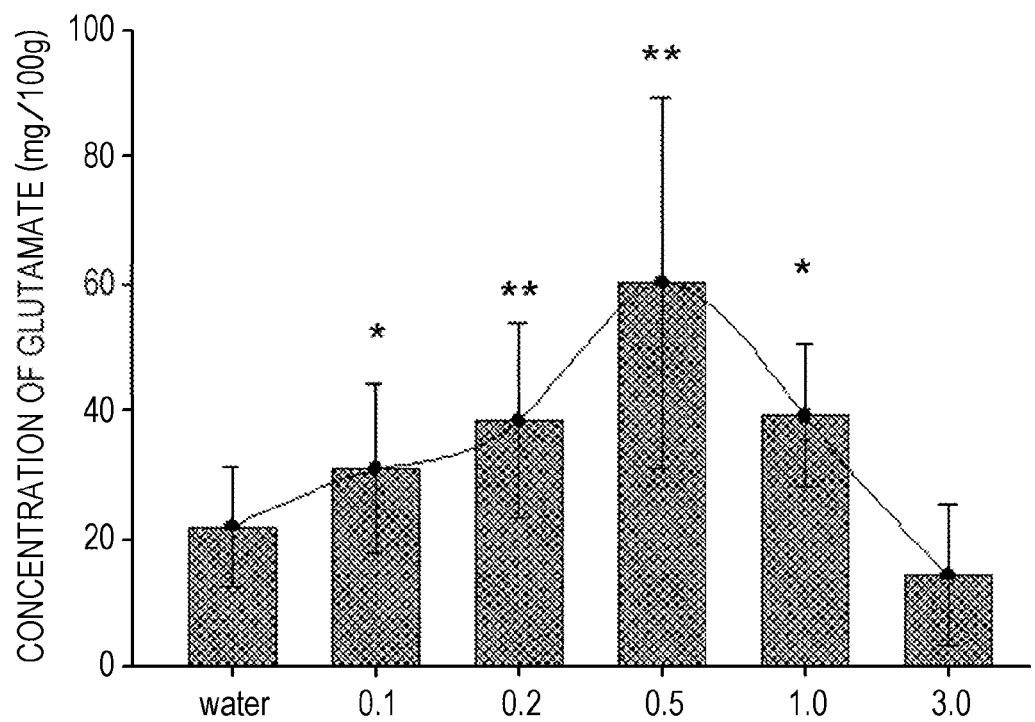
FIG. 1 is a graphical representation of the results on the glutamate content of cereals.

A characteristic feature of the sprouted cereal of the present invention is to be obtained by soaking the cereal in a soaking solution prepared by addition of at least one carbonate selected from a group consisting of alkali metal carbonate, alkaline earth metal carbonate, and ammonium carbonate to water to make the cereal absorb the soaking solution, followed by allowing the cereal to germinate under predetermined conditions.

The soaking solution used in the present invention is prepared by addition of alkali metal carbonate such as sodium carbonate, sodium bicarbonate, sodium sesquicarbonate, potassium carbonate, or potassium bicarbonate; alkaline earth metal carbonate such as calcium carbonate or calcium bicarbonate; or ammonia carbonate such as ammonium carbonate or ammonium hydrogen carbonate to water. Any of them provides a predetermined concentration of hydrocarbon ion. Among them, in particular, sodium carbonate, sodium bicarbonate, and sodium sesquicarbonate are preferably used.

The germination technique of the present invention as well as a food product raw material or a pharmaceutical agent, which can obtained by the germination technique, employs a method including soaking or immersing a cereal in an aqueous alkaline solution containing at least a predetermined concentration of sodium bicarbonate to make the cereal germinate.

The aqueous solution containing at least sodium bicarbonate used in the germination process can be obtained by dissolving sodium bicarbonate power, sodium carbonate power, or sodium sesquicarbonate powder (a blend of sodium bicarbonate and sodium carbonate: $NaHCO_3 \cdot Na_2CO_3 \cdot 2H_2O$) in water. However, combinations of these ingredients, an adjusting method therefor, and the like are not specifically limited.

The concentration of sodium bicarbonate in the aqueous solution containing at least sodium bicarbonate, which aims to enrich glutamate of the present invention, is preferably in the range of 0.1 to 3.0 mass %, or more preferably 0.1 to 1.0 mass %. For example, less than 0.1 mass % is not preferred. This is because, if the sodium bicarbonate concentration is less than 0.1 mass %, the pH of the aqueous solution becomes 8.0 or lower at a weak alkaline or neutral range. Such conditions are suitable for the growth of microorganisms, so that an effect of reducing the germination-specific smell can be insufficient. In contrast, more than 1.0 mass % is not preferred. This is because, if the sodium bicarbonate concentration exceeds 1.0 mass %, a sproutable food material, such as cereals, is colored, and thus the sodium bicarbonate concentration of more than 3.0% leads to suppression of a germination reaction.

If the concentration of the aqueous solution containing at least including sodium bicarbonate, which aims to accelerate an enrichment of gamma-aminobutyric acid of the present invention, is less than 0.1 mass %, for example, the PH value of the aqueous solution becomes 8.0 or less at a weak alkaline or neutral range. Thus, less than 0.1 mass % is not preferred. This is because, such conditions are suitable for the growth of microorganisms and thus an effect of reducing the germination-specific smell can be insufficient. In contrast, more than 0.5 mass % is not preferred. This is because, a decrease in enhancement of gamma-aminobutyric acid progresses. For accelerating an enrichment of gamma-aminobutyric acid, the concentration of sodium bicarbonate is preferably in the range of 0.1 to 0.5 mass %.

The conditions of the "aqueous solution containing at least sodium bicarbonate" for immersing or soaking a sproutable food material therein may be those of an aqueous solution that enriches glutamate to accelerate an enrichment of gamma-aminobutyric acid, and causes an expression of functionality of accelerating the production of BDNF in the body by administration of the food material. Thus, the solution may include other ingredients such as minerals, proteins, amino acids, carbohydrates, and lipids. Note that the pH of the aqueous solution used for germination should be in the range of 8.0 to 11, preferably 8.0 to 10.

When an aqueous sodium bicarbonate solution is prepared at ordinary temperature an sodium bicarbonate ingredient in the aqueous solution gradually changes to sodium carbonate. In the aqueous sodium bicarbonate solution, the entire composition of sodium bicarbonate at the time of preparation is not kept as it is. Specifically, it changes to an aqueous sesquisodium carbonate solution, which is an aqueous solution provided as a mixture of sodium bicarbonate with sodium carbonate. However, the present invention is based on the results obtained by adjusting an initial concentration of sodium bicarbonate at the time of preparing he aqueous solution (Examples described below) Therefore, the initial (calculated) concentration of sodium bicarbonate at the time of preparing the aqueous solution may be within the above range. A subsequent chronological change in composition of the aqueous solution in the strict sense of the word is not specifically limited.

The soaking conditions and other conditions for water supply are not specifically limited as long as the duration of contact enriches glutamate in a sproutable food material, accelerates an enrichment of gamma-aminobutyric acid, and causes an expression of functionality of accelerating the production of BDNF in the body. The amount of water for soaking, immersing, or the like on a moment-to-moment basis is not specifically limited. For example, when the temperature of the solution is in the range of 15 to 40° C., the duration of soaking or immersion is in the range of 12 to 84 hours. Preferably, when the temperature of the solution is in the range of 20 to 35° C., the duration of soaking or immersion is in the range of 24 to 72 hours. More preferably, when the temperature of the solution is in the range of 25 to 30° C., the duration of soaking or immersion is in the range of 36 to 60 hours.

According to the present invention, in comparison with the conventional germination method, the content of glutamate and the content of gamma-aminobutyric acid can be highly enriched. In addition, an unprecedented memory enhancement effect, an unprecedented appetite suppression (weight suppression) effect, and an wait-suppression effect, which are involved (or may be involved) in a sproutable food material, can be extensively accelerated. Any smell generated from a sproutable food material can be reduced by germination with an aqueous solution containing a predetermined concentration of sodium bicarbonate but not merely with water (fresh water or tap water). Although the reason is not clear, one of the materials is known to absorb a sodium bicarbonate ingredient to exert a deodorizing effect. In addition, the bacteriostatic and anti-microbial effects of the aqueous solution containing a sodium bicarbonate ingredient may suppress the growth of microorganisms causing the generation of smells and being attached to the surface of a sproutable food material.

The solution with more than a certain concentration of sodium bicarbonate is at alkaline pH, including bases. Therefore, one more reason, in addition to the above description, is the lipid elements on the surface of the food ingredients with germination properties, which are the trophic factor for the microorganisms, are easily removed (cleaned) after the combination with bases (alkaline elements in the solution) via a saponification mechanism.

The germination using an aqueous solution containing at least a certain amount of sodium bicarbonate but not using water (pure water or tap water) enriches glutamate, a delicious taste ingredient, and accelerates an enrichment of gamma-aminobutyric acid as described in the examples below. However, the reason thereof is not clear. Conventionally, as described above, an aqueous sodium bicarbonate solution has been only known to exert suppressive effects on the germination rate and growth of plant.

It has been already known that sodium bicarbonate has suppressive effects on the growth of plant in general. In general, living creatures have natural properties for enhancing their viabilities (physical natures) in response to some "growth suppressive environments", which are so-called springs for them, and for living more powerfully. An aqueous sodium bicarbonate solution within the concentration range specified in the present invention may become an environment for "appropriate suppression" of the growth of plant to allow the plant to adjust its inner reaction patterns and obtain various kinds of additional properties and functionality. So far, it has not been reported that an aqueous solution containing a certain concentration of sodium bicarbonate can allow a sproutable food material to express entirely new functionality, an acceleration of BDNF production in the body, and it has not been disclosed the reason of such expression.

The accelerated BDNF production in the body is expected to cause preferably functionality, such as a nerve/synapse formation promoting action, a motor paralysis restoring action, a cerebral function disorder improving action, a brain protecting action, an improving action for late effects of cerebral stroke, a peripheral neuropathy improving action, a mitogenic action for neural stem cells, an improving action for cognitive or memory ability, an antiobesity action, an appetite suppressing action, a glucose-metabolism improving action, a fat metabolism improving action, an antidepressant action, an antianxiety action, a listless improving action, a pain relief action, an improving action for generative function, an accelerating action for fertilized ovum maturity, an improving action for fertility index, an improving action for erectile function disorder, an accelerating action for epithelial keratitis cell proliferation, a fair skin action, a regulating action for epithelial function, an accelerating action for hair follicle cell regeneration, a hair growth action, an immune-competence regulating action, and a life extending action. In other words, the use of the sprouted brown rice of the present invention can be expected to express these preferable functions.

The BDNF production accelerator of the present invention can be used as pharmaceutical agents, such as a nerve/synapse formation promoting agent, a motor paralysis restoring agent, a cerebral function disorder improving agent, a brain protecting agent, an improving agent for late effects of cerebral stroke, a peripheral neuropathy improving agent, a mitogenic agent for neural stem cells, an improving agent for cognitive or memory ability, an antiobesity agent, an appetite suppressing agent, a glucose-metabolism improving agent, a fat metabolism improving agent, an antidepressant agent, an antianxiety agent, a listless improving agent, a pain relief agent, an improving agent for generative function, an accelerating agent for fertilized ovum maturity, an improving agent for fertility index, an improving agent for erectile function disorder, an accelerating agent for epithelial keratitis cell proliferation, a fair skin agent, a regulating agent for epithelial function, an accelerating agent for hair follicle cell regeneration, a hair growth agent, an immune-competence regulating agent, and a life extending agent. The BDNF production accelerator of the present invention can be also used as a raw material for drinking food products, such as nutraceuticals (supplements), healthy food products, healthy drinks, modified milk for baby, baby foods and artificial feeding and supplements thereof, and nutraceutical foods and supplements thereof.

A sproutable food material is soaked or immersed in an aqueous solution containing at least sodium bicarbonate, and then germinated. Subsequently, the sprouted food material is placed under low temperature conditions of 10° C. or lower or is dried to suppress or terminate a germination reaction. However, depending on the applications of the present invention, it is not always required for the termination of germination.

The term "sproutable food material" used herein refers to, for example, rice, brown rice or wheat, which is eaten as a main food staple; a food material used as a side dish or a seasoning; a food material used as a ferment material, such as brewing or pickles; a food material used as a beverage material or an additive, a food material used as a livestock food; and any of food materials used for other applications, which include cereals, seeds, root vegetables, and stumps.

The types of cereals are not specifically limited. Examples of cereals include brown rice, glutinous rice, red rice, black rice, Indica rice, Javanica rice, pea, broad beans, black soybeans, parched beans, adzuki beans, snap (kidney) beans, safflower kidney beans, peas, peanuts, black soybeans, soybeans, corn, buckwheat, mochi-mugi (glutinous wheat), oats, millet, Italian millet, proso millet, mocha-awa (glutinous millet), Japanese millet, and mochi-kibi (glutinous proso millet). The terms "wheat" and "corn" are used for food products, brewing, or the like. The terms imply barley, wheat, oats, young corns, and white corns. However, their types and species are not specifically limited.

Examples of the sproutable food material described in the present invention include sproutable plants, such as seeds, root crops, and stumps, but not specifically limited thereto.

For example, the plants include sesame, black sesame, white sesame, kin-goma (gold sesame), radish, carrots, Irish potato, sweet potato, and yam (family), secondary taro corm, ginger plant, garlic, lotus roots, onion, lily root, mulberry, Japanese jam, taro, red stock, turnip, nozawana, new share, Edible burdocks, bean sprouts, sunflower seed, peanuts, macadamia nut, almond, walnuts, cacao beans, and coffee beans.

Furthermore, the sproutable food material used in the present invention may include an embryo bud portion, or may only include the embryo bud portion. Alternatively, the plant may be whole rice or partially polished rice. Rice with husk or shell or none of them may be subjected to germination. Alternatively, cereals or seeds may be of early harvesting, which are harvested earlier than usual, for example blue brown rice.

The germination method of the present invention reduces a smell, enriches glutamate or gamma-aminobutyric acid, or accelerates an enrichment thereof, and accelerates the production of BDNF in the body. Thus, the germination method of the present invention can be used for the purpose of producing sprouted cereals, such as sprouted barley and sprouted soybean, which can be provided as fermentation raw materials of alcoholic beverage, bean paste, soy sauce, and the like.

The germination method of the present invention can be used in the production of sprouted brown rice or sprouted cereals and tea for the purpose of extracting their effective ingredients and performing administration of the resulting extract. This is because the method is capable of reducing smell, enriching glutamate, accelerating an enrichment of gamma-aminobutyric acid, and accelerating the production of BDNF in the body by administrating a product thus obtained.

Examples of dosage forms of the "internal BDNF production accelerator" of the present invention include, but not specifically limited to, peroral formulations such as tablets, powders, emulsions, capsules, granules, fine granules, powdered medicines, liquid medicines, syrups, suspensions, and elixirs. Moreover, the "internal BDNF production accelerator" may contain an additional ingredient. Alternatively, it may be combined with a food product such as rice, soy sauce, soybean paste, pickled products, tea, cacao beans, cocoa, chocolate, coffee, drinking water, alcoholic drinks.

The internal BDNF production accelerator of the present invention can be orally administered, accelerating the BDNF production in the body. As a result, the following expected advantages are obtained: The brain becomes strong enough to endure various stresses or obtains strong mentality, thereby reducing anxiety, aggressiveness, and brutality. In other words, the administration of the intracerebral BDNF enhancer of the present invention to a human without regardless of age, gender, and species, any of various kinds of mammals, or any of other animals lead to enhance the survivability of the brain, stabilize mentality, enhance fertility, and extend lifetime (the rest of life).

The internal BDNF production accelerator or the food product of the present invention can enhance vitality, reduce anxiety/aggressiveness/brutality, and enhance the longevity, so that it can be used in the purpose to reduce aggressiveness/brutality, or extend lifetime (the rest of life) of various kinds of animals in addition to humans.

The present invention will be described with reference to the following examples. However, the present invention is not limited to these examples.

Example 1

Production of Sprouted Brown Rice Using Aqueous Sodium Bicarbonate Solution

Aqueous sodium bicarbonate solutions (pH 8.0 to 1.0 at room temperature) were prepared by dissolving predetermined amounts of edible sodium bicarbonate powder in amounts of 0.1, 0.2, 0.5, 1.0, and 3.0 mass % (i.e., hydrogen carbonate ion levels of 0.012, 0.024, 0.06, 0.12, and 0.36 mol/l) in five liters of water. Brown rice harvested by a farmer in Mino city (Osaka, Japan), 2 kg, was immersed in each of the resulting solutions and water of equivalent volume for 24 hours (i.e., water-absorption process). Subsequently, the brown rice was collected from the solution or the water, and then placed on and wrapped by disposal paper towel (Kimtowel®) moist with the solution or the water in a metal tray in a room at 25° C. Thus, the brown rice was in contact with both air and moisture at room temperature, thereby keeping its wet condition (i.e., germination process). The germination process was terminated when the germination rate of the brown rice reached more than 80% (the sprout was determined by the growth length, at least for 0.5 to 1.0 mm) or after a laps of 84 hours regardless of the germination rate. After the termination of the germination process, the brown rice was placed in a room set at 4° C. and left drying for 3 days in the room to reduce the moisture content of the brown rice down to about 10% (i.e., drying process). Consequently, the sprouted brown rice of interest was obtained.

[Evaluation 1]

Glutamate Content Measurement 1

Twenty samples (50 g each) were obtained from the germinated rice obtained in Example 1.

Using a quantitative glutamate assay kit (available from Yamasa soy sauce, Co. Ltd. under the trade name Yamasa L-glutamate assay kit), the absolute level of glutamate content of the samples were determined as follows: Hydrogen peroxide generated by reaction of L-glutamate oxidase with glutamate in the sample was subjected to peroxidase reaction (coloring with blue) with substrates, 4-aminoantipyrine and DAOS, followed by subjecting to quantitative analysis with colorimetry to make a comparison test with a standard value. Each sample was assayed in triplicate or more, and the average value was used.

The results are shown in FIG. 1. In the figure, "water" represents the sprouted brown rice germinated in pure water, and the numerical values [0.1 to 3.0] indicate the concentrations (mass %) of sodium bicarbonate in the aqueous sodium bicarbonate solution used for the germination process.

As in evident from the results in FIG. 1, the glutamate content of the sprouted brown rice vary with the concentrations of sodium bicarbonate in the aqueous sodium bicarbonate solution. When the concentration of sodium bicarbonate was more than 0.1 mass % (hydrogen carbonate ion>0.012 mol/l), the glutamate content were significantly higher than those in the samples germinated in water as control ($P<0.05$, One-way ANOVA).

[Evaluation 2]

Glutamate Content Measurement 2

The glutamate contents of commercially available brown rice (using the average value of four different products; the product from Awaji-shima in Hyogo prefecture, Mino city in Osaka prefecture, Sanda city in Hyogo prefecture, or the product from Akita prefecture) and commercially available sprouted brown rice produced by the conventional method (using the average value of the different five products; Anan-sprouted brown rice, sprouted rough brown rice, Fukuren-sprouted brown rice, and Koi-Azusa sprouted brown rice with 28-fold GABA, and FANCL sprouted brown rice) were compared with the glutamate content of the sprouted brown rice produced in Example 1 in which the solution with 0.2 mass % of the aqueous sodium bicarbonate solution (hydrogen carbonate ion concentration=0.024 mol/l) was used. The measurement method used was the same described above. The results are shown in FIG. 2, in which the abbreviation "Brown" represents the average value from the commercially available brown rice (four different types), "PGR" represents the average value from the commercially available sprouted brown rice (five different types), and "PGR-SB" represents the product obtained in Example 1 germinated using the aqueous sodium bicarbonate solution.

Figure 2:
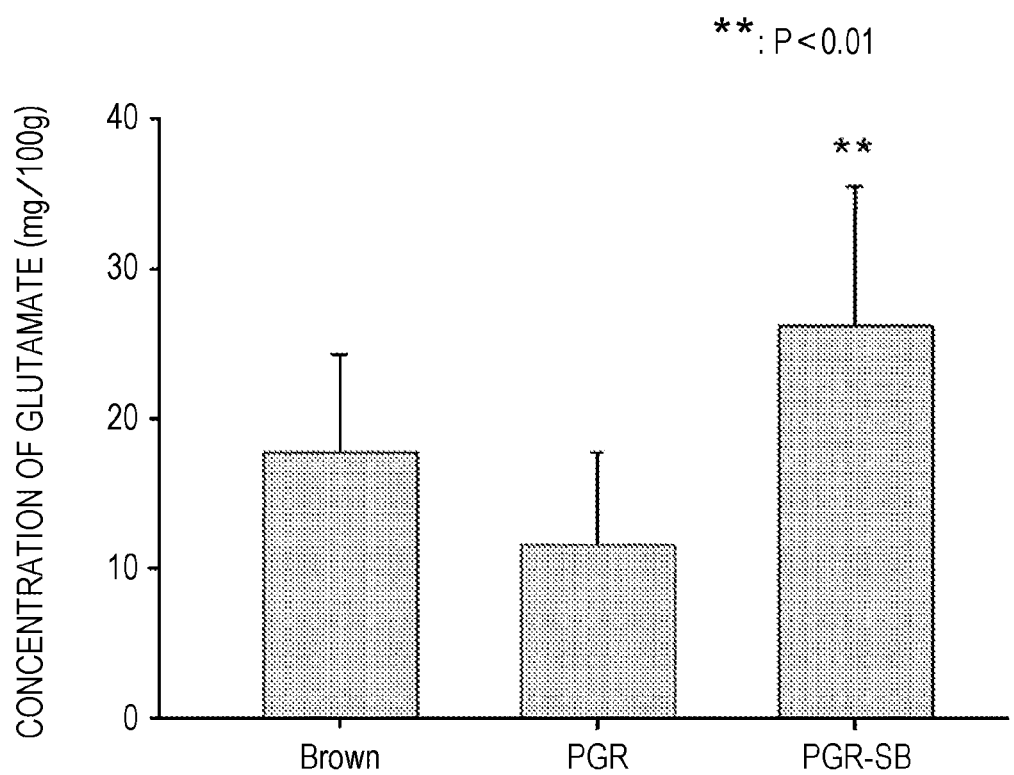
FIG. 2 is a graphical representation of the results on the glutamate content of cereals.

As is evident from the results in FIG. 2, the glutamate content of the commercially available sprouted brown rice produced by the conventional method was lower compared to the glutamate content of the commercially available brown rice. However, the glutamate content of the sprouted brown rice germinated in the aqueous sodium bicarbonate solution of Example 1 was statistically significant and higher than the glutamate content of the sprouted brown rice produced by the conventional germination method ($P<0.01$, One-way ANOVA). In summary, it was found that the germination method of the present invention could enhance the glutamate content of sprouted brown rice compared to the conventional method.

Comparative Example 1

Production of Sprouted Brown Rice Using the Extract of Tea Leaves (Glutamate-Containing Solution)

Sprouted brown rice was obtained by almost the same manner as that of Example 1, except that 4.5 mass % of a tea leaf extract containing a large amount of glutamate, which was extracted from tea leaves (1.0 mass % in water) using hot water, was added instead of the edible sodium bicarbonate powder.

[Evaluation 3]
Glutamate Content Measurement 3

Figure 3:
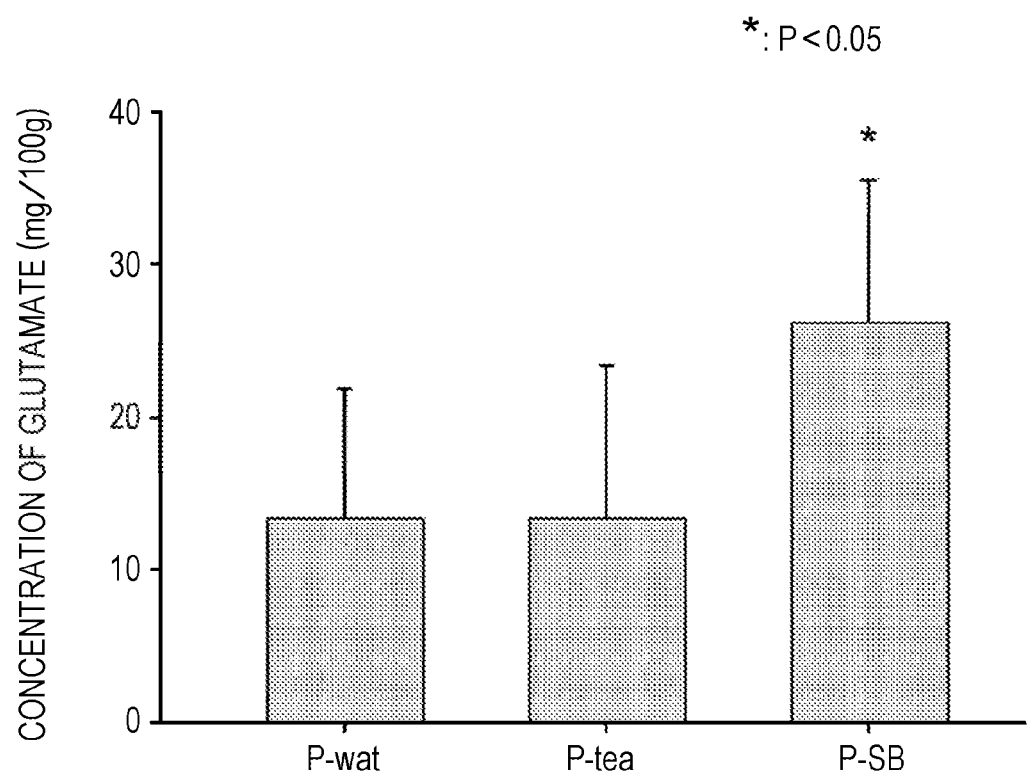
FIG. 3 is a graphical representation of the results on the glutamate content of cereals.

The glutamate content of the sprouted brown rice obtained in Comparative Example 1 was measured by the above measurement method, and then compared with the results of the sprouted brown rice obtained using the aqueous solution of 0.2-mass % sodium bicarbonate (0.024 mol/l in hydrogen carbonate ion concentration) and the results of the sprouted brown rice obtained using pure water in Example 1. The results are shown in FIG. 3. In addition, "P-wat" in the figure represents the sprouted brown rice germinated in pure water, "P-tea" represents the sprouted brown rice germinated using the extract of tea leaves (glutamate-containing solution). Furthermore. "P-SB" represents sprouted brown rice germinated in an aqueous sodium bicarbonate solution obtained in Example 1.

As is evident from the results in FIG. 3, the glutamate content of the sprouted brown rice produced by addition of the glutamate-containing solution was not higher than the glutamate content of the sprouted brown rice germinated in pure water. However, the glutamate content of the sprouted brown rice germinated in the aqueous sodium bicarbonate solution of Example 1 was statistically significant and was higher than the glutamate content of glutamate of the sprouted brown rice germinated in the glutamate-containing solution ($P<0.05$, One-way ANOVA). That is, the content of gamma-aminobutyric acid, which was produced using glutamate as a raw material, was enriched by the germination method using pure water or the germination method using the glutamate-containing solution, but could not enrich the content of glutamate more than the original content of glutamate in the raw material. However, it was found that the germination method of the present invention could just enrich glutamate.

Example 2

Production of Sprouted Barley, Sprouted Wheat, Sprouted Kin-Goma, Sprouted Black Bean, Sprouted Soybean Sprouted barley, sprouted wheat, sprouted Kin-Goma, sprouted black bean, and sprouted soybean of interest were obtained by almost the same manner as that of Example 1, except that barley (Shunrai), wheat, Kin-Goma (golden sesame), black bean, and soybean were used instead of the brown rice and they were germinated using a the aqueous solution of 0.2-mass % sodium bicarbonate (0.024 mol/l in hydrogen carbonate ion concentration) and using pure water as control.

[Evaluation 4]
Glutamate Content Measurement 4

The glutamate contents of the sprouted barley, sprouted wheat, sprouted Kin-Goma, sprouted black bean, and sprouted soybean generated using the aqueous sodium bicarbonate solution and the pure water, which are obtained in Example 2, were measured by the above measurement method, respectively. The results are shown in FIG. 4.

Figure 4:
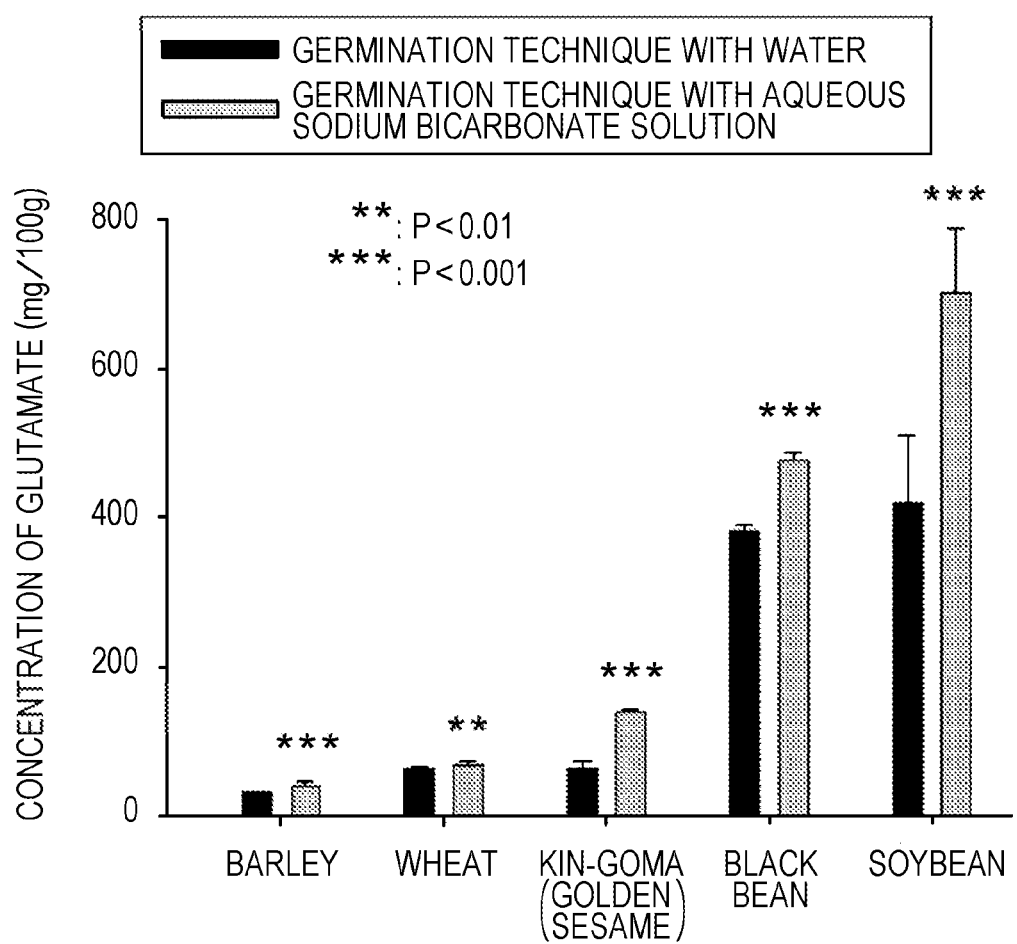
FIG. 4 is a graphical representation of the results on the glutamate content of cereals.

As is evident from the results in FIG. 4, the glutamate content of the sprouted cereal germinated in the glutamate-containing solution was statistically significant and higher than the glutamate content of the conventional sprouted cereal germinated in pure water. That is, it was found that the sprouted cereals of the present invention could significantly enrich glutamate compared with one using the typical water even in the case of using cereals (barley, wheat, black bean, and soybean) and seeds (Kin Goma in Pedaliaceae) other than brown rice ($P<0.05$, t-test).

[Evaluation 5]
Gamma-Aminobutyric Acid Content Measurement 1

Twenty samples (50 g each) were obtained from the sprouted brown rice in Example 1.

The measurement of gamma-aminobutyric acid content in the samples was performed based on a technique described in the Japanese Patent Application No 2008-106488 and developed at the International Research Center of Agriculture.

Figure 5:
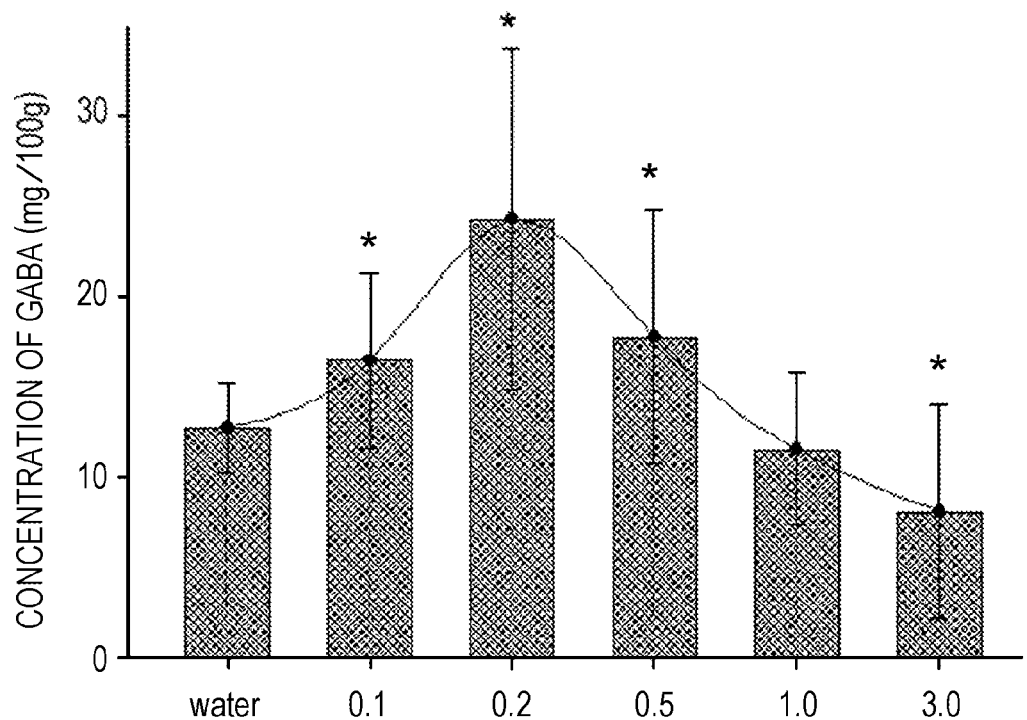
FIG. 5 is a graphical representation of the results on the gamma-aminobutyric acid content of cereals.

The results of the measurement are shown in FIG. 5. In the figure, "Water" represents the sprouted brown rice germinated in pure water, and the numerical values "0.1 to 3.0" represent the concentration (mass %) of the aqueous sodium bicarbonate solution used in the germination process.

As is evident from the results in FIG. 5, the gamma-aminobutyric acid content of the sprouted brown rice varied with the concentrations of the aqueous sodium bicarbonate solution used in germination. It was found that, in the case of using the aqueous sodium bicarbonate solution at concentrations of 0.1 to 0.5 mass %, the gamma-aminobutyric acid was significantly enriched compared with the method using the typical water in germination ($P<0.05$, One-way ANOVA).

[Evaluation 6]
Gamma-Aminobutyric Acid Content Measurement 2

The gamma-aminobutyric acid content of the brown rice (using the average value of four different products described in Evaluation 2), and the commercially available sprouted brown rice produced by the conventional method (using the average value of the different five products described in the evaluation 2) were measured by the above measurement method, and then compared with the results of the sprouted brown rice produced in Example 1 using the aqueous solution of 0.2-mass % sodium bicarbonate (0.024 mol in hydrogen carbonate ion concentration). The results are shown in FIG. 6, in which the abbreviation "Brown" represents the average value from the commercially available brown rice (four different types), "PGR" represents the average value from the commercially available sprouted brown rice (five different types), and "PGR-SB" represents the sprouted brown rice germinated in the aqueous sodium bicarbonate solution in Example 1.

Figure 6:
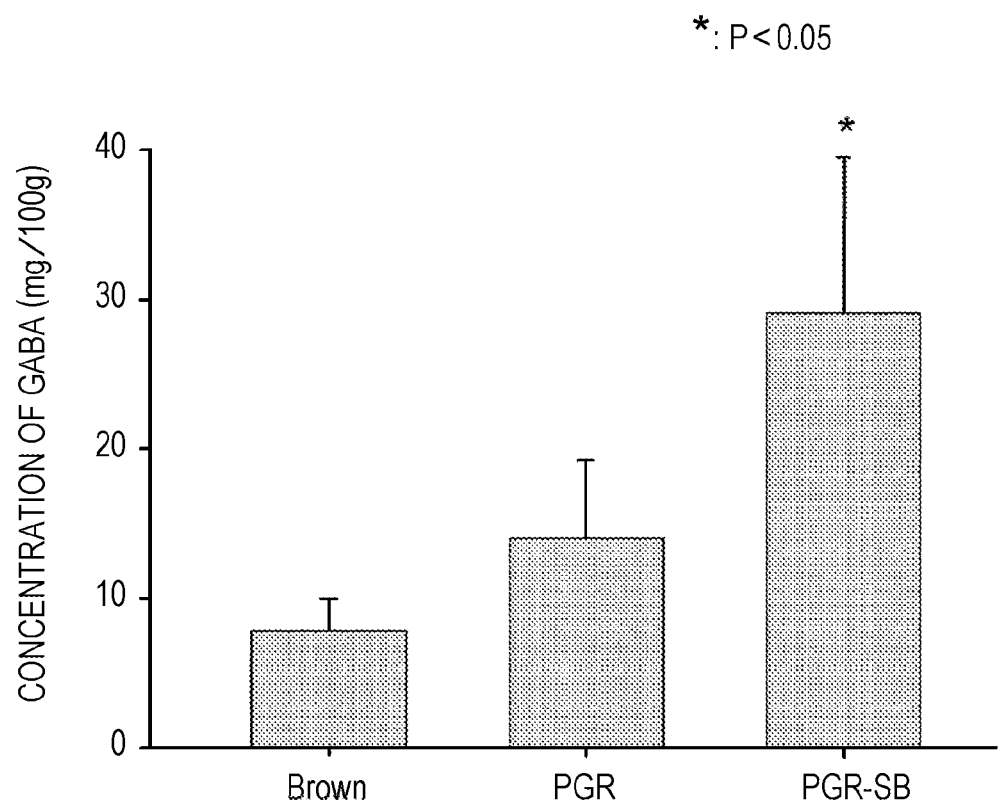
FIG. 6 is a graphical representation of the results on the gamma-aminobutyric acid content of cereals.

As is evident from the results in FIG. 6, the gamma-aminobutyric acid content of the sprouted brown rice was statistically significant and higher than the gamma-aminobutyric acid content of the commercially available brown rice or sprouted brown rice. In summary, it was found that the germination method of the present invention could significantly enhance an enrichment of gamma-aminobutyric acid compared with the conventional germination method ($P<0.05$, One-way ANOVA).

[Evaluation 7]
Gamma-Aminobutyric Acid Content Measurement 3

The gamma-aminobutyric acid contents of the sprouted brown rice, white rice, and brown rice (using rice grown in Awaji-Island, the brand name; Kinuhikari), which were germinated using the tea leaf extract (glutamate-containing solution) obtained in Comparative Example 1, were measured by the above method. The results of the measurement were compared with the results of the sprouted brown rice produced in Example 1 using the aqueous solution of 0.2-mass % sodium bicarbonate (0.024 mol/l in hydrogen carbonate ion concentration). The results are shown in FIG. 7, in which the abbreviation "White" represents the white rice, "Brown" represents the brown rice, "P-wat" represents the sprouted brown rice germinated in pure water, "P-tea" represents the sprouted brown rice germinated in the tea leaf extract (glutamate-containing solution), and "P-SB" represents the sprouted brown rice germinated in the aqueous sodium bicarbonate solution.

Figure 7:
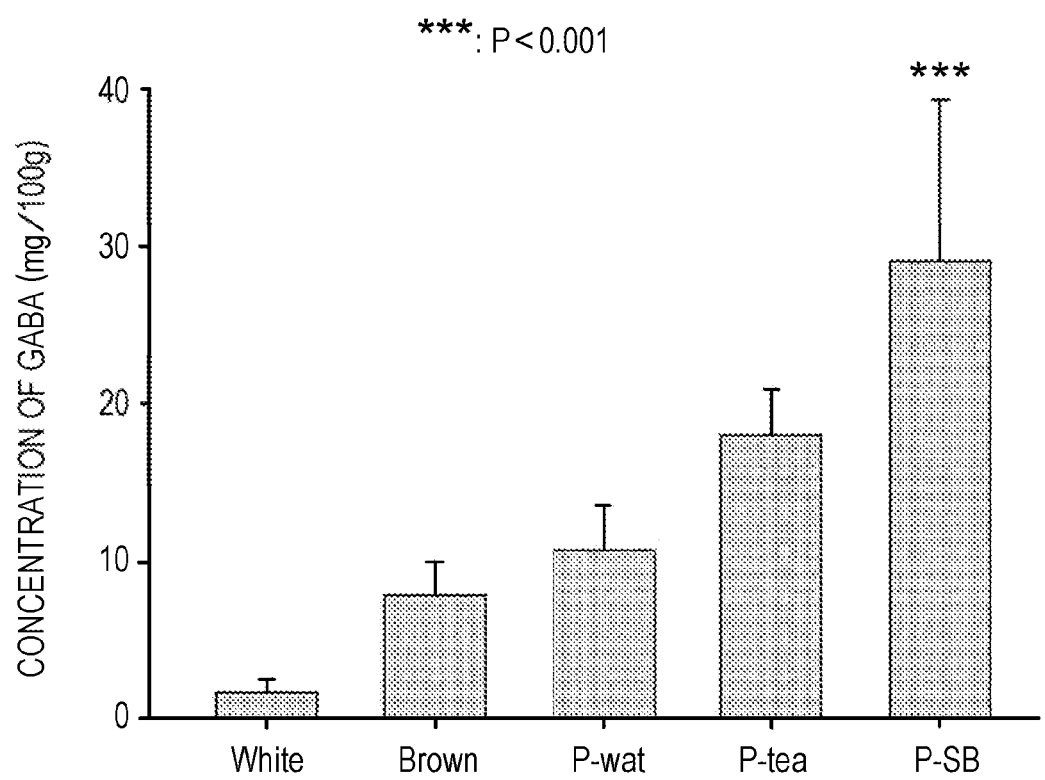
FIG. 7 is a graphical representation of the results on the gamma-aminobutyric acid content of cereals.

As is evident from the results in FIG. 7, the gamma-aminobutyric acid content of the sprouted brown rice was significantly higher than the gamma-aminobutyric acid content of the white rice, brown rice, or the sprouted brown rice using water or tea leaves. In summary, it was found that the germination method of the present invention could significantly enhance gamma-aminobutyric acid compared with the method using water or the glutamate-containing solution ($P<0.001$, One-way ANOVA).

[Evaluation 8]
Gamma-Aminobutyric Acid Content Measurement 4

The gamma-aminobutyric acid contents of the sprouted barley, sprouted wheat, sprouted Kin-Goma (golden sesame), sprouted black bean, or sprouted soybean, which were germinated in the aqueous sodium bicarbonate solution and the pure water in Example 2, were measured by the above measurement method. The results are shown in FIG. 8.

Figure 8:
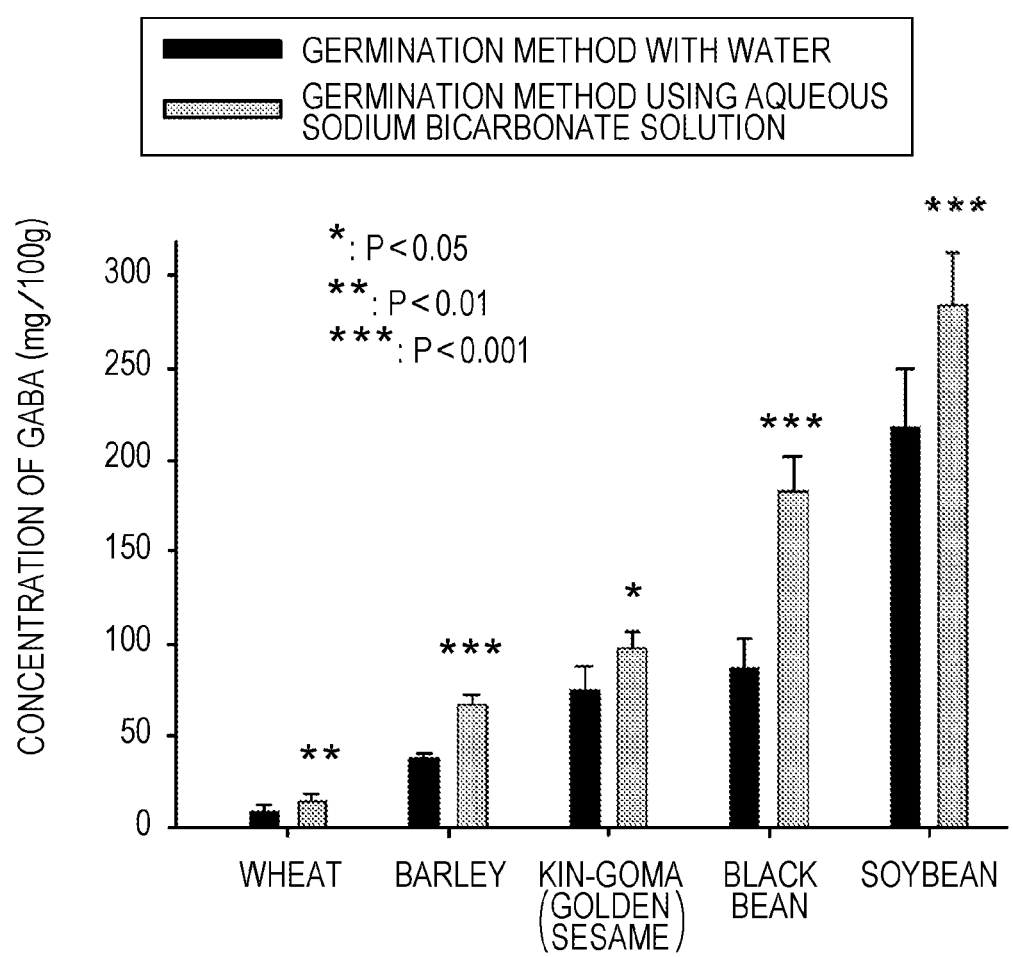
FIG. 8 is a graphical representation of the results on the gamma-aminobutyric acid content of cereals.

As is evident from the results in FIG. 8, it was found that the gamma-aminobutyric acid content in the germination method using the aqueous sodium bicarbonate solution in germination could be higher than the gamma-aminobutyric acid content in the germination method using the pure water in germination. That is, it was found that the sprouted cereals of the present invention could significantly enriching gamma-aminobutyric acid compared with one using the typical water even in the case of using cereals (barley, wheat, black bean, and soybean) and seeds (Kin Goma in Pedaliaceae) other than brown rice ($P<0.01$, t-test).

[Evaluation 9]
Evaluation of Suppression of Increase in Body Weight

The sprouted brown rice germinated in the aqueous solution of 0.2-mass % sodium bicarbonate (0.024 mol/l in hydrogen carbonate ion concentration) and the sprouted brown rice germinated in the pure water, which were obtained in Example 1; the sprouted brown rice germinated in the extract tea leaves (glutamate-containing solution), which was obtained in Comparative Example 1: and two different types of commercially available sprouted brown rice (Koiazusa: 28-fold GABA sprouted brown rice or sprouted brown rice produced by FANCL Co. Ltd.) were respectively administered for 6 weeks to male C57BL/6J mice (7-week old, 10 to 20 per group). The results are shown in FIG. 9, in which the abbreviation "P-A" represents the 28-fold GABA sprouted, "P-B" represents the FANCL sprouted brown rice, "P-wat" represents the sprouted brown rice germinated in pure water, "P-tea" represents the sprouted brown rice germinated in a tea leaf extract (glutamate-containing solution), and "P-SB" represents the sprouted brown rice germinated in the aqueous sodium bicarbonate solution.

Figure 9:
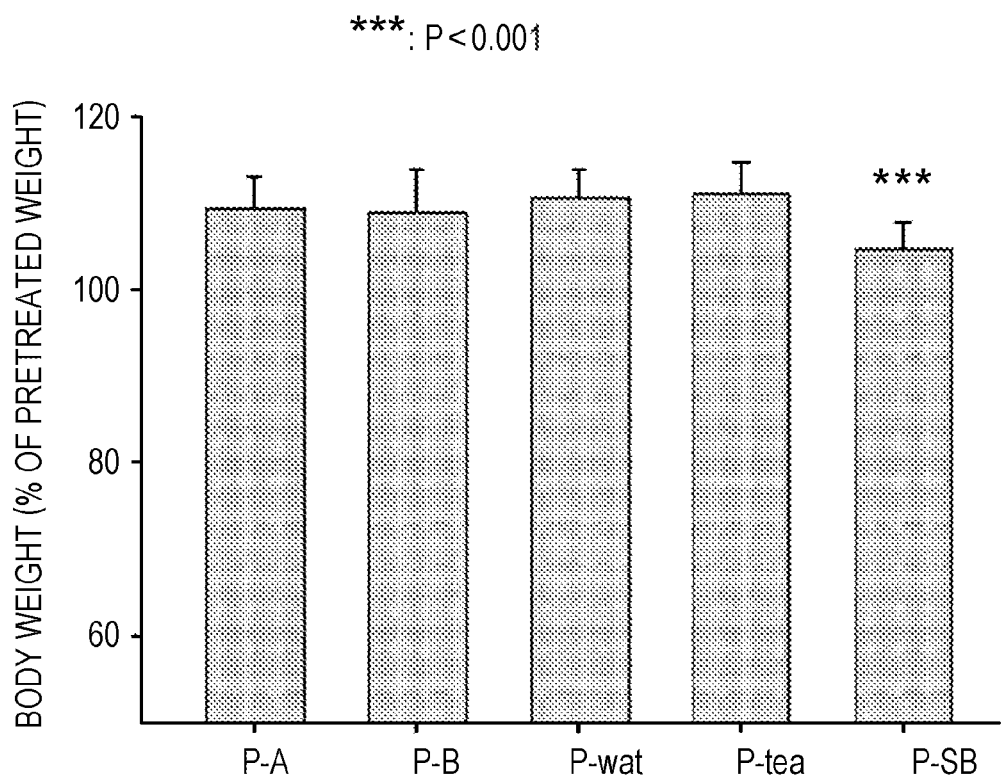
FIG. 9 is a graphical representation of the results of evaluation on the inhibitory effect on an increase in body weight.

As is evident from the results in FIG. 9, the group administered with the sprouted brown rice generated in the aqueous sodium bicarbonate solution of Example 1 showed significant suppression of body weight gain, compared with the group administered with the commercially available sprouted brown rice A, the commercially available sprouted brown rice B, and the sprouted brown rice germinated in the water or the tea leaf extract (glutamate-containing solution). In summary, it was found that the germination method of the present invention could have a significant effect of suppression of body weight gain, compared to the conventional germination method or another germination method ($P<0.001$, One-way ANOVA).

[Evaluation 10]
Evaluation of Property on Improvement of Glucose/Lipid Metabolism The sprouted brown rice germinated in the aqueous solution of 0.2-mass % sodium bicarbonate (0.024 mol/l in hydrogen carbonate ion concentration) and the sprouted brown rice germinated in pure water, which were obtained in Example 1, were administered for 6 weeks to male C57BL/6J mice (7-week old, 10 per group), respectively. The sprouted brown rice was then subjected to measurement of biological indications in the blood, HDL (so called "good or beneficial cholesterol") or LDL (so called "bad cholesterol") and blood glucose levels. The results are indicated in FIG. 10, in which the abbreviation "HDL" represents a level of high-density lipoprotein, "LDL" represents a level of low-density lipoprotein, and "Glu" represents a blood glucose level.

Figure 10:
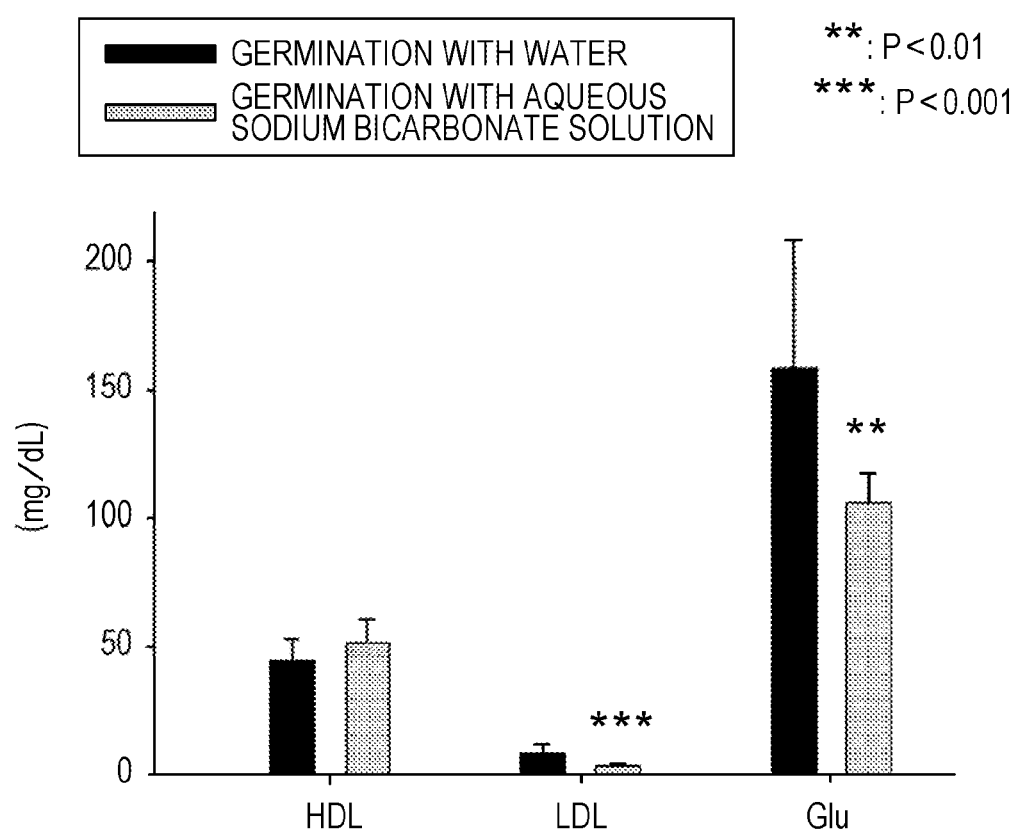
FIG. 10 is a graphical representation of the results of evaluation on glucose/lipid metabolism improving effects.

As is evident from the results in FIG. 10, the group administered with the sprouted brown rice germinated in the aqueous sodium bicarbonate solution of Example 1 showed a comparatively higher HDL value and significantly lower LDL and blood levels, compared with the sprouted brown rice germinated in the pure water. In summary, It was found that the continuous administration of the sprouted brown rice manufactured by the germination method of the present invention had improvement effects on glucose/lipid metabolism, compared with the continuous administration of the sprouted brown rice manufactured by the germination method using the typical water. ($P<0.01$, t-test).

[Evaluation 11]
Evaluation of Property on Enhancement of Memory Function

The sprouted brown rice germinated in the aqueous solution of 0.2-mass % sodium bicarbonate (0.024 mol/l in hydrogen carbonate ion concentration) and the sprouted brown rice germinated in pure water, which were obtained in Example 1, and brown rice (all of them were "Kinuhikari" from Awaji-Island) were administered for 6 weeks to male C57B/J6J mice (7-week old, 11 per group), respectively. After completing the administration period, the spatial memory function was evaluated using the water maze test as described below.

The water maze test is performed as follows: A predetermined size water bath is filled with turbid water so that the depth of water can be enough to prevent the mice from standing up in the bath. Then each mouse is placed in a predetermined position in the water bath. Because the mouse hates to stay in the bath, it swims to find a place to stand up safely. After a certain period, the mouse can reach a small platform (a sole foothold on which the mouse can stand up) hidden in the water. By repeating the attempt, the mouse learns the place of the platform using the view around the pool, and reaches the platform in shorter periods of time. Four attempts (sessions) per day are repeated for five days in the water maze test, and the total running (swam) distance in each session in each mouse was calculated using an image analysis software. When the swimming distance to reach the hidden platform is decreased, the mouse is considered to have obtained a better memory function. The results are shown in FIG. 11, in which the abbreviation "Brown" represents the brown rice, "P-wat" represents the sprouted brown rice germinated in the pure water, and "P-SB" represents the sprouted brown rice germinated in the aqueous sodium bicarbonate solution.

Figure 11:
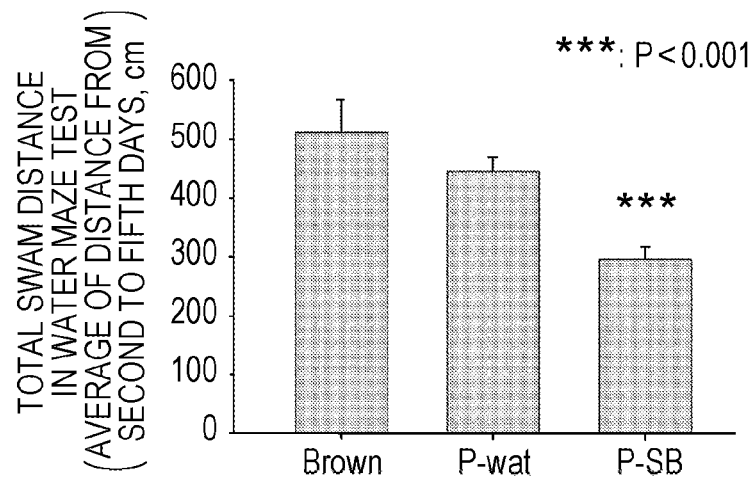
FIG. 11 is a graphical representation of the results of evaluation on memory enhancing effects.

As is evident from the results in FIG. 11, the group administered with the sprouted brown rice germinated in the aqueous sodium bicarbonate solution of Example 1 shows a shorter total distance from the dropping point to the safe platform in a statistically significant manner, compared with the sprouted brown rice germinated in the pure water and the brown rice ($P<0.001$, One-way ANOVA). In summary, it was found that the germination method of the present invention could significantly improve the properties of spatial perception and mneme to express functionality, compared with the conventional germination method using water.

[Evaluation 12]
Evaluation of Anti-Depressive Property

The sprouted brown rice germinated in the aqueous solution of 0.2-mass % sodium bicarbonate (0.024 mol/l in hydrogen carbonate ion concentration), which was obtained in Example 1, and commercially available sprouted brown rice (Anan) were administered for five weeks to male C57BL6J mice (7-week old, 11 per group). After completing the administration period, the groups were respectively subjected to a forced swim test as described below to evaluate the degree of depression onset.

The forced swim test is performed as follows: A water bath in the form of a cylindrical tube of 10 cm in diameter was filled with water so that the depth of water can be enough to prevent the mice from standing up in the bath. Then, the mouse is placed in the water bath for 15 minutes. After 24 hours later, the mouse is placed in the water bath for 5 minutes, while the total time period of body motion of 2 cm/second or more (climbing, avoiding behavior from danger) is analyzed using a behavior analysis software. The results are shown in FIG. 12, in which the abbreviation "P-SB" represents the sprouted brown rice germinated in the aqueous sodium bicarbonate solution, and "P" represents the commercially available sprouted brown rice.

Figure 12:
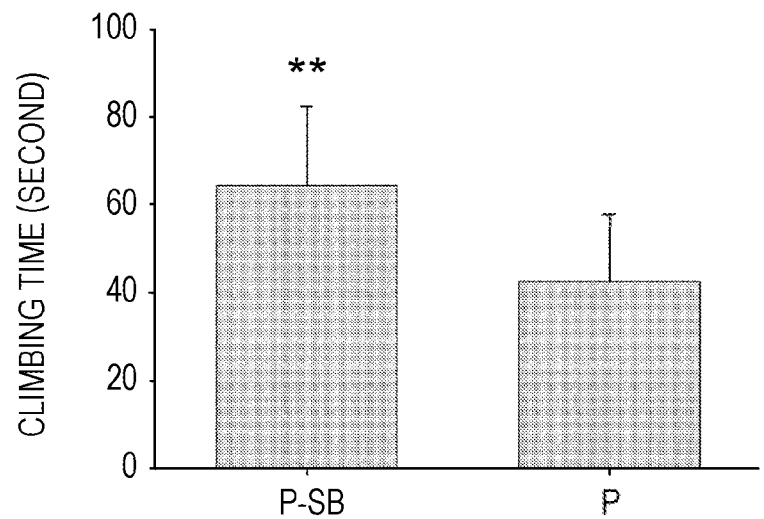
FIG. 12 is a graphical representation of the results of evaluation on anti-depression effects.

As is evident from the results in FIG. 12, the group administered with the sprouted brown rice germinated in the aqueous sodium bicarbonate solution of Example 1 showed a prolonged climbing time, compared with the group administered with the commercially available sprouted brown rice, in a statistically significant manner ($P<0.01$ t-test). In summary, it was found that the germination method of the present invention could suppress the onset of depression, compared with the conventional germination method.

[Evaluation 13]
Evaluation of Enhancing Property of BDNF Production

The sprouted brown rice germinated in the aqueous solution of 0.2-mass % sodium bicarbonate (0.024 mol/l in hydrogen carbonate ion concentration) obtained in Example 1, the brown rice (grown in Awaji-Island, Kinuhikari-brand), and the commercially sprouted brown rice (three different types of sprouted brown rice: Anan sprouted brown rice, Inochi sprouted brown rice, and Koiazusa 28-fold GABA sprouted brown rice) were administered for 6 weeks to male C57BLJ6J mice (7-week old, 16 per group). After completing the administration, the groups were respectively subjected to the ELISA method to determine the intracerebral BDNF levels of the mice. The results are shown in FIG. 13, in which the abbreviation "Brown" represents the brown rice, and "A", "B", and "C" respectively represent the commercially available sprouted brown rice, and "D" represents the sprouted brown rice germinated in the aqueous sodium bicarbonate solution.

Figures 13, 14:
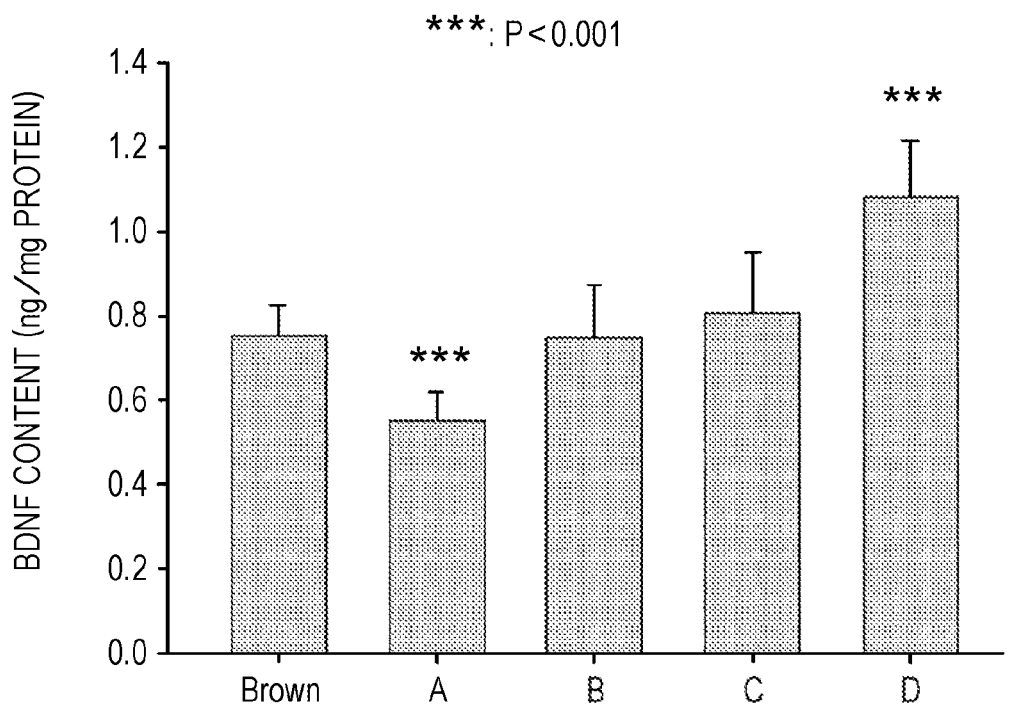
FIG. 13 is a graphical representation of the results of evaluation on BDNF production-enhancing effects.
FIG. 14 is a graphical representation of the results of evaluation on taste sensation.

As is evident from the results in FIG. 13, the group administered with the sprouted brown rice (D) germinated in the aqueous sodium bicarbonate solution of Example 1 showed a higher intracerebral BDNF level, compared with the brown rice (Brown), in a statistically significant manner ($P<0.001$, One-way ANOVA). On the other hand, in the case of the intracerebral BDNF levels of the groups administered with the commercially available sprouted brown rice (A to C), the sprouted brown rice (A) showed a significantly small change, and the sprouted brown rice (B) and (C) did not show any significant change. In summary, the group after administration of the sprouted brown rice by the germination method of the present invention showed a statistically significant increase in intracerebral BDNF level, compared with the group administered with the brown rice. In contrast, the commercially available sprouted brown rice (A to C) using the conventional germination method showed a significant decrease in intracerebral BDNF level, but not showed a significant increase in intracerebral BDNF level.

[Evaluation 14]
Evaluation of Taste

The sprouted brown rice germinated in the aqueous solution of 0.2-mass % sodium bicarbonate (0.024 mol/l in hydrogen carbonate ion concentration) and the sprouted brown rice germinated in the pure water, which were obtained in Example 1, were similarly cooked using a household electric rice cooker. A sensory evaluation for taste was performed on nine test subjects (persons in their teens to seventies) who were not informed of the manufacturing method. Evaluation items were "tasty (umami)" and "flavor". A three grade evaluation, 1 (unfavorable), 2 (difficult to judge), and 3 (excellent), was performed. The results of the taste sensory evaluation are shown in FIG. 14.

As is evident from the results in FIG. 14, the sprouted brown rice germinated in the aqueous sodium bicarbonate solution in Example 1 showed higher scales of the umami and the flavor, compared with the sprouted brown rice germinated in the pure water, in a statistically significant manner (*: P<0.05, t-test).

In summary, it was shown that the sprouted brown rice of the present invention were superior in the umami and flavor scale, compared with the sprouted brown rice germinated in the conventional water.

Comparative Example 2

Production of Sprouted Brown Rice Using Aqueous Sodium Hydroxide Solution and Bittern Sprouted brown rice of interest was obtained in a manner similar to Example 1, except that an aqueous solution of 0.2-mass % dilute sodium hydroxide (pH 8.2 to 8.4) and 0.05, 0.1, 0.2, and 0.5 mass % of "bittern" (including cations such as sodium, potassium, calcium, and magnesium; and anions such as fluorine, chlorine, and bromine) were used instead of the aqueous sodium bicarbonate solution.
[Evaluation 15]
Glutamate Content Measurement 5 and Gamma-Aminobutyric Acid Content Measurement The sprouted brown rice germinated in the aqueous dilute sodium chloride solution obtained in Comparative Example 2 and the sprouted brown rice germinated in bittern were subjected to the above measurement to determine their glutamate content and gamma-aminobutyric acid content. The results were then compared with the results of the sprouted brown rice obtained using the aqueous solution of 0.2-mass % sodium bicarbonate (0.024 mol/l in hydrogen carbonate ion concentration) and the sprouted brown rice obtained using the pure power in Example 1. The results are shown in FIGS. 15 and 16, in which the abbreviation "P-SB" represents the sprouted brown rice obtained in Example 1 using the aqueous sodium bicarbonate solution, "pH" represents the sprouted brown rice germinated in the aqueous dilute sodium chloride solution, and numerals "0.05 to 0.5" represent the concentrations (mass %) of the bittern used.

Figure 15:
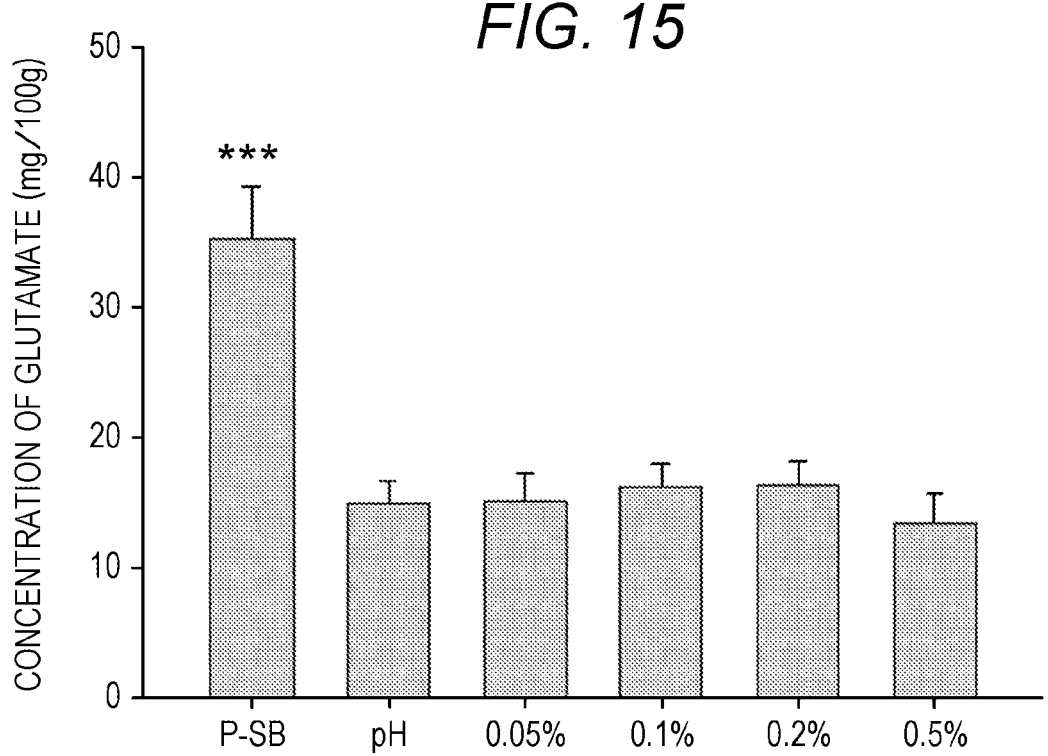
FIG. 15 is a graphical representation of the results of glutamate content measurement.
Figure 16:
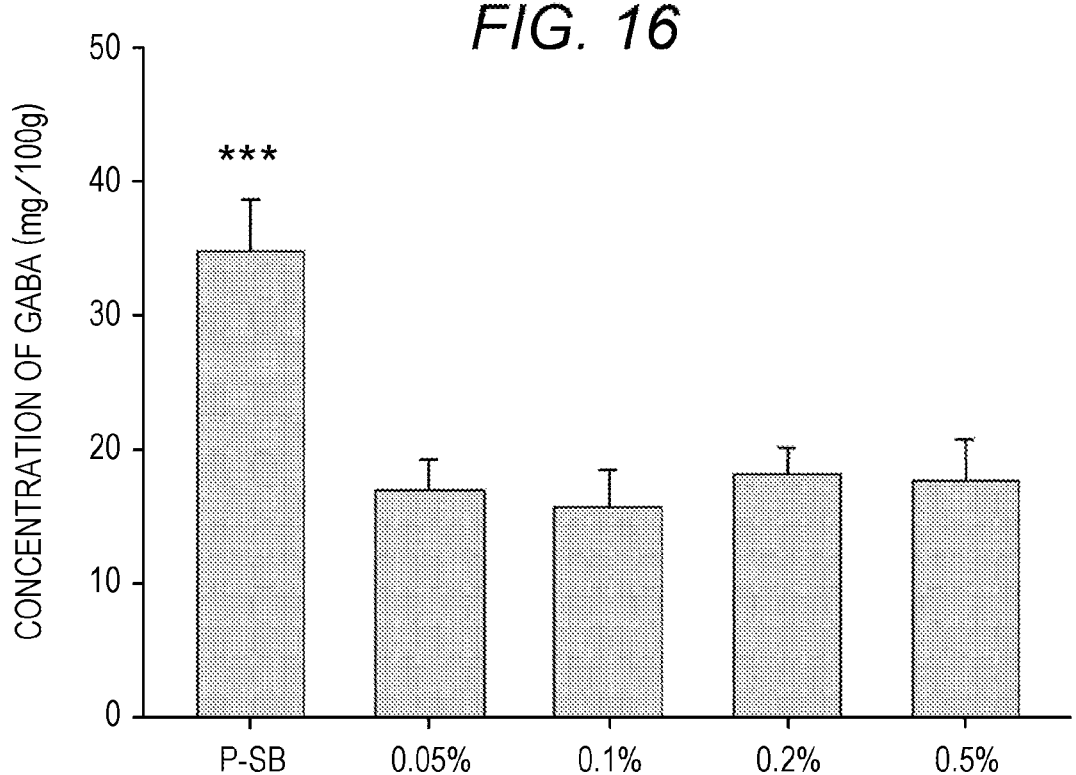
FIG. 16 is a graphical representation of the results of gamma-aminobutyric acid content measurement.

As is evident from the results in FIGS. 15 and 16, the glutamate content and gamma-aminobutyric acid content of the sprouted brown rice germinated in the aqueous sodium bicarbonate solution were higher than those of the sprouted brown rice germinated only in another pH-adjusted solution or the sprouted brown rice germinated in the various concentration-adjusted aqueous ionic solutions in a statistically significant manner.

In summary, it was found that the germination method of the present invention cannot be substituted with the only pH-adjusted aqueous solution and various concentration-adjusted aqueous ionic solution, and requires the characteristics of an aqueous solution containing at least hydrocarbon ion (***: P<0.001, One-way ANOVA)

INDUSTRIAL APPLICABILITY

The method for manufacturing a sproutable food material of the present invention is excellent in degree of purity/sanitation with respect to the growth of microorganisms and also excellent in flavor, taste (umami, flavor), and functionality, while being performed in comparatively lost cost. Thus, the method can be used in various kinds of food products or food raw materials or beverages in which sproutable food materials are used as their raw materials.

A process for germinating cereals or the like may be included in fermentation and brewing, such as the production of beer and other alcohol drinks. Thus, the method of the present invention can be also used for the purpose of expressing the functionality of these final products, improving delicious taste, and improving flavor taste.

The food product for acceleration of internal BDNF production of the present invention accelerates the production of BDF in the body. Thus, the food product can be produced as a health food product or a pharmaceutical agent that intends to cause an increase in internal BDNF, an enhancement of mneme (improvement of dementia), a suppression of appetite (reduction of excessive body weight), an increase in viability of neural cells, an increase in resistivity against fetal stress, prevention of cerebral infarction (inhibition of brain damages), moderation of brutality/aggression, improvement of depressive mood (depressive symptoms), an enhancement of a beautiful skin effect, an enhancement of hair augmentation, augmentation an increase in fertility, and an improvement in longevity.

Furthermore, the sproutable food material or the internal BDNF enhancer having these functions can be used in various kinds of animals and organisms including humans. Thus, it can be used for the purpose of improving memory/learning ability, enhancing health, adjusting body shape, elongating life, increasing fertility, or suppressing aggressiveness/brutality.

Furthermore, the germination method having the above functions suppresses the growth of microorganisms during the germination process. Such a method also serves as a foster/growth method that increases the glutamate content and gamma-aminobutyric acid content (amino acid–synthesizing ability=cytoskeleton–synthesizing ability=the growth ability), or increases the vitality and growing ability of plants. Thus, if the plant grows up without stopping these germination reactions subsequent to the initial stage of germination, the plant can be expected to be strong against disorders and harmful insects, and to give harvests such as plentiful fruits, rhizomes, seeds, bulbs or the like. In summary, an aqueous solution in the range of 0.1 to 0.5 mass % and having pH of 8.0 to 10.0 may be sprayed on the agricultural land or used instead of another environmental water to provide a plant that can be expected to be grown up to reduce an influence of microorganisms. Thus, the plant can be provided with more enhancing viability, while giving more harvests.

The invention claimed is:
1. A sprouted cereal selected from a group consisting of soybean, bean, sesame, barley, and wheat, produced by soaking the cereal in a soaking solution having a hydrogen carbonate ion to make the cereal absorb the soaking solution, followed by allowing the cereal to germinate under predetermined conditions.
2. The sprouted cereal according to claim 1, wherein pH of the soaking solution ranges from 8.0 to 10.0.
3. The sprouted cereal according to claim 1, wherein a concentration of the hydrogen carbonate ion in the soaking solution is 0.012 to 0.06 mol/l.
4. The sprouted cereal according to claim 3, wherein a gamma-aminobutyric acid content of the sprouted cereal is 1.3 to 2.1 times greater than a gamma-aminobutyric acid content of a sprouted cereal germinated under the same conditions except that the latter is germinated without addition of the hydrogen carbonate, when measured by a reference measurement method.
5. The sprouted cereal according to claim 3, wherein a glutamate content of the sprouted cereal is 1.1 to 2.3 times greater than a glutamate content of a sprouted cereal germinated under the same conditions except that the latter is germinated without addition of the hydrogen carbonate, when measured by a reference.

6. A food product comprising the sprouted cereals according to claim 1.

7. A method for producing the sprouted cereal of claim 1, the method comprising the steps of:
    soaking the cereal in a soaking solution having the hydrogen carbonate ion to make the cereal absorb the soaking solution; and
    allowing the cereal absorbing the soaking solution in the previous step to germinate under predetermined conditions.

8. The method for producing the sprouted cereal of claim 7, wherein
    pH of the soaking solution ranges from 8.0 to 10.0.

9. The method for producing the sprouted cereal of claim 7, wherein
    a concentration of the hydrogen carbonate ion in the soaking solution is 0.012 to 0.06 mol/l.

10. The method for producing the sprouted cereal of claim 9, wherein
    a gamma-aminobutyric acid content of the sprouted cereal is 1.3 to 2.1 times greater than a gamma-aminobutyric acid content of a sprouted cereal germinated under the same conditions except that the latter is germinated without addition of the hydrogen carbonate, when measured by a reference measurement method.

11. The method for producing the sprouted cereal of claim 9, wherein
    a glutamate content of the sprouted cereal is 1.1 to 2.3 times greater than a glutamate content of a sprouted cereal germinated under the same conditions except that the latter is germinated without addition of the hydrogen carbonate, when measured by a reference measurement method.

* * * * *